(12) United States Patent
Duffy et al.

(10) Patent No.: US 9,579,197 B2
(45) Date of Patent: Feb. 28, 2017

(54) SYSTEMS AND METHODS FOR POSITIONING A HEART VALVE USING VISUAL MARKERS

(75) Inventors: Niall Duffy, Ballyglyunin (IE); Gerry McCaffrey, Ballybrit (IE); Noam Miller, Netanya (IL); Yossi Tuval, Netanya (IL); Daniel Glozman, Kefar Adummim (IL)

(73) Assignee: Medtronic Vascular, Inc., Santa Rosa, CA (US)

( * ) Notice: Subject to any disclaimer, the term of this patent is extended or adjusted under 35 U.S.C. 154(b) by 960 days.

(21) Appl. No.: 13/325,439

(22) Filed: Dec. 14, 2011

(65) Prior Publication Data

US 2012/0158129 A1 Jun. 21, 2012

Related U.S. Application Data

(60) Provisional application No. 61/423,386, filed on Dec. 15, 2010.

(51) Int. Cl.
*A61F 2/24* (2006.01)
*A61F 2/95* (2013.01)

(52) U.S. Cl.
CPC .......... *A61F 2/2427* (2013.01); *A61F 2/2436* (2013.01); *A61F 2002/9505* (2013.01); *A61F 2250/0032* (2013.01); *A61F 2250/0097* (2013.01); *A61F 2250/0098* (2013.01)

(58) Field of Classification Search
CPC ...... A61F 2250/0032; A61F 2250/0097; A61F 2250/0098; A61F 2/2427; A61F 2/95; A61F 2/966; A61F 2/97; A61F 2002/9505; A61F 2002/9511; A61F 2002/9534; A61F 2002/9665; A61F 2002/011; A61F 2/00; A61F 2002/0072
USPC ............................ 623/1.11, 2.11, 2.12, 2.17
See application file for complete search history.

(56) References Cited

U.S. PATENT DOCUMENTS

| 5,709,703 A | * | 1/1998 | Lukic et al. | 623/1.12 |
| 6,285,903 B1 | * | 9/2001 | Rosenthal et al. | 600/433 |
| 7,044,966 B2 | * | 5/2006 | Svanidze et al. | 623/2.1 |
| 7,320,704 B2 | * | 1/2008 | Lashinski et al. | 623/2.11 |

(Continued)

FOREIGN PATENT DOCUMENTS

| GB | 2398245 | 8/2004 |
| WO | WO2005-002466 | 1/2005 |

(Continued)

*Primary Examiner* — Eric Rosen
*Assistant Examiner* — Lucas Paez

(57) ABSTRACT

A valve retainer is connected to an elongate delivery member. The valve retainer is configured to releasably secure a prosthesis (e.g., a heart valve prosthesis) to the delivery member during delivery to a target site in a body (e.g., a native valve annulus). The valve retainer includes a rotational identifier that identifies the rotational orientation of the valve retainer when the valve retainer is positioned proximate to the target site. A heart valve prosthesis can include a commissural post that has a predetermined rotational position relative to the rotational identifier, such that the heart valve prosthesis can be rotationally aligned with the native commissures of the native valve by rotating the delivery member and the valve retainer until the commissural post is aligned with a native valve commissure and the rotational identifier is visible.

15 Claims, 11 Drawing Sheets

(56) References Cited

U.S. PATENT DOCUMENTS

| | | | |
|---|---|---|---|
| 7,381,219 B2* | 6/2008 | Salahieh et al. | 623/2.11 |
| 8,236,049 B2* | 8/2012 | Rowe et al. | 623/2.11 |
| 2001/0049549 A1* | 12/2001 | Boylan | A61F 2/95 |
| | | | 623/1.11 |
| 2005/0197695 A1 | 9/2005 | Stacchino et al. | |
| 2006/0149360 A1 | 7/2006 | Schwammenthal et al. | |
| 2008/0071345 A1* | 3/2008 | Hammersmark et al. | 623/1.11 |
| 2008/0071361 A1 | 3/2008 | Tuval et al. | |
| 2008/0071366 A1 | 3/2008 | Tuval et al. | |
| 2008/0071368 A1 | 3/2008 | Tuval et al. | |
| 2008/0071369 A1 | 3/2008 | Tuval et al. | |
| 2009/0099650 A1* | 4/2009 | Bolduc et al. | 623/1.36 |
| 2010/0121436 A1 | 5/2010 | Tuval et al. | |
| 2010/0131054 A1 | 5/2010 | Tuval et al. | |
| 2010/0137979 A1 | 6/2010 | Tuval et al. | |
| 2010/0262231 A1 | 10/2010 | Tuval et al. | |

FOREIGN PATENT DOCUMENTS

| | | |
|---|---|---|
| WO | WO2006/070372 | 7/2006 |
| WO | WO2010/031060 | 3/2010 |

* cited by examiner

SYSTEMS AND METHODS FOR POSITIONING A HEART VALVE USING VISUAL MARKERS

This application claims the benefit of U.S. Provisional Application No. 61/423,386, filed Dec. 15, 2010, the entire disclosure of which is incorporated in its entirety herein by reference thereto.

BACKGROUND OF THE INVENTION

Field of the Invention

The present invention relates generally to prosthetic heart valves, and specifically to techniques for accurately positioning such valves during implantation procedures.

Background

Aortic valve replacement in patients with severe valve disease is a common surgical procedure. The replacement is conventionally performed by open heart surgery, in which the heart is usually arrested and the patient is placed on a heart bypass machine. In recent years, prosthetic heart valves have been developed which are implanted using minimally invasive procedures such as transapical or percutaneous approaches. These methods involve compressing the prosthesis radially to reduce its diameter, inserting the prosthesis into a delivery tool, such as a catheter, and advancing the delivery tool to the correct anatomical position in the heart. Once properly positioned, the prosthesis is deployed by radial expansion within the native valve annulus.

While these techniques are substantially less invasive than open heart surgery, the lack of line-of-sight visualization of the prosthesis and the native valve presents challenges because the physician cannot see the actual orientation of the prosthesis during the implantation procedure. Correct positioning of the prosthesis is achieved using radiographic imaging, which yields a two-dimensional image of the viewed area. The physician must interpret the image correctly in order to properly place the prostheses in the desired position. Failure to properly position the prosthesis can lead to device migration or to improper functioning. Proper device placement using radiographic imaging is thus important to the success of the implantation.

PCT Publication WO 05/002466 to Schwammenthal et al., which is incorporated herein by reference, describes prosthetic devices for treating aortic stenosis.

PCT Publication WO 06/070372 to Schwammenthal et al., which is incorporated herein by reference, describes a prosthetic device having a single flow field therethrough, adapted for implantation in a subject, and shaped so as to define a fluid inlet and a diverging section, distal to the fluid inlet.

U.S. Patent Application Publication 2006/0149360 to Schwammenthal et al., which is incorporated herein by reference, describes a prosthetic device including a valve-orifice attachment member attachable to a valve in a blood vessel and including a fluid inlet, and a diverging member that extends from the fluid inlet, the diverging member including a proximal end near the fluid inlet and a distal end distanced from the proximal end. A distal portion of the diverging member has a larger cross-sectional area for fluid flow therethrough than a proximal portion thereof.

U.S. Patent Application Publication 2005/0197695 to Stacchino et al., describes a cardiac-valve prosthesis adapted for percutaneous implantation. The prosthesis includes an armature adapted for deployment in a radially expanded implantation position, the armature including a support portion and an anchor portion, which are substantially axially coextensive with respect to one another. A set of leaflets is coupled to the support portion. The leaflets can be deployed with the armature in the implantation position. The leaflets define, in the implantation position, a flow duct that is selectably obstructable. The anchor portion can be deployed to enable anchorage of the cardiac-valve prosthesis at an implantation site.

U.S. Patent Application Publication 2010/0121436 ("the '436 publication") to Tuval et al., which is incorporated, herein in its entirety by reference, describes a heart valve with three commissural posts and a delivery system therefore. During implantation, the valve prosthesis, including the commissural posts, is initially collapsed within a delivery tube. Before expanding the valve prosthesis, a physician uses radiographic imaging, such as x-ray fluoroscopy, to provide visual feedback that aids the physician in rotationally aligning the commissural posts with respective native commissures of a native semilunar valve. The identifiers strongly contrast with the rest of the commissural posts and the valve prosthesis, which comprise a radiopaque material. Without such identifiers, it is generally difficult to three-dimensionally visually distinguish the commissural posts from one another and from the rest of the valve prosthesis, because the radiographic imaging produces a two-dimensional representation of the three-dimensional valve prosthesis. When the valve prosthesis is in a collapsed state, the elements thereof overlap in a two-dimensional image and are generally indistinguishable.

The '436 publication describes a procedure during which the physician selects one of the commissural posts having a radiographic identifier, and attempts to rotationally align the selected post with one of the native commissures, such as the commissure between the left and right coronary sinuses. Because the radiographic image is two-dimensional, all of the posts appear in the image as though they are in the same plane. The physician thus cannot distinguish between two possible rotational positions of the posts: (1) the desired rotational position, in which the selected post faces the desired native commissure, and (2) a rotational position 180 degrees from the desired rotational position, in which the selected post faces the side of the native valve opposite the desired native commissure. For example, if the desired native commissure is the commissure between the left and right coronary sinuses, in position (2) the post is rotationally aligned with the non-coronary sinus, although this undesired rotation is not apparent in the radiographic image. To ascertain whether the posts are in rotational position (1) or (2), the physician slightly rotates the valve prosthesis. If the radiographic identifier on the selected post appears to move in the radiographic image in the same direction as the rotation, the selected post is correctly rotationally aligned in the desired position (1). If, on the other hand, the radiographic identifier appears to move in the direction opposite the direction of rotation, the selected post is incorrectly rotationally aligned in position (2). To correct the alignment, the physician may rotate the valve prosthesis approximately 60 degrees in either direction, thereby ensuring that one of the two other posts is now rotationally aligned in position (1).

BRIEF SUMMARY OF THE INVENTION

Heart valve prostheses and systems and methods of delivering heart valve prostheses are provided. The delivery systems and methods herein seek to simplify implantation of heart valve prostheses by reducing the amount of time and the number of steps necessary to implant prostheses. A heart valve prosthesis can include three commissural posts to which are coupled a prosthetic valve. The commissural posts can be shaped so as define therethrough respective openings that serve as radiographic identifiers during an implantation procedure. During the procedure, the valve prosthesis, including the commissural posts, is initially collapsed within a delivery tube. Before expanding the valve prosthesis, a physician uses radiographic imaging, such as x-ray fluoroscopy, to provide visual feedback that aids the physician in rotationally aligning the commissural posts with respective native commissures of a native semilunar valve. The identifiers strongly contrast with the rest of the commissural posts and the valve prosthesis, which comprise a radiopaque material. Without such identifiers, it is generally difficult to three-dimensionally visually distinguish the commissural posts from one another and from the rest of the valve prosthesis, because the radiographic imaging produces a two-dimensional representation of the three-dimensional valve prosthesis. When the valve prosthesis is in a collapsed, state, the elements thereof overlap in a two-dimensional image and are generally indistinguishable.

A valve retainer is connected to an elongate delivery member, wherein the valve retainer is configured to releasably secure the prosthesis to the elongate delivery member during delivery to a target site in a body. The valve retainer includes a rotational identifier configured to allow a user to identify the rotational orientation of the valve retainer, and thereby the rotational orientation of the commissural posts of the prosthesis, when the valve retainer is positioned proximate to the target site in the body.

The physician selects one of the comimissural posts having a radiographic identifier, and attempts to rotationally align the selected post with one of the native commissures, such as the commissure between the left and right coronary sinuses. Because the radiographic image is two-dimensional, all of the posts appear in the image as though they are in the same plane. The physician thus cannot distinguish between two possible rotational positions of the posts: (1) the desired rotational position, in which the selected post faces the desired native commissure, and (2) a rotational position 180 degrees from the desired rotational position, in which the selected post faces the side of the native valve opposite the desired native commissure. For example, if the desired native commissure is the commissure between the left and right coronary sinuses, in position (2) the post is rotationally aligned with the non-coronary sinus, although this undesired rotation is not apparent in the radiographic image.

To ensure proper rotational alignment, a fluoroscopic image of the heart valve prosthesis, the valve retainer, and the native valve commissures is generated. The heart valve prosthesis is then rotationally aligned by rotating the elongate delivery member and the valve retainer until a commissural post is aligned with a native valve commissure and the rotational identifier is visible on a predetermined side of the valve retainer such that the rotational position of the commissural post with respect to the rotational identifier is known.

The present invention will be more fully understood from the following detailed description of embodiments thereof, taken together with the drawings.

DETAILED DESCRIPTION OF THE INVENTION

The following detailed description of heart valve prostheses and systems and methods of delivering heart valve prostheses refers to the accompanying figures that illustrate exemplary embodiments. Other embodiments are possible. Modifications can be made to the embodiments described herein without departing from the spirit and scope of the present invention. Therefore, the following detailed description is not meant to be limiting. Further, it would be apparent that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented. For example, while the description provided is directed to heart valve prostheses and systems and methods of delivering heart valve prostheses, the systems and methods described herein should not be limited to delivery of heart valve prostheses. One of skill in the art would readily understand how to incorporate the features and structures described herein into delivery systems and methods for other types of prostheses. For example, the systems and methods described herein can be used for other types of procedures, such as delivery of stents, valves, or other prostheses to a variety of areas in the body.

Figure 1:
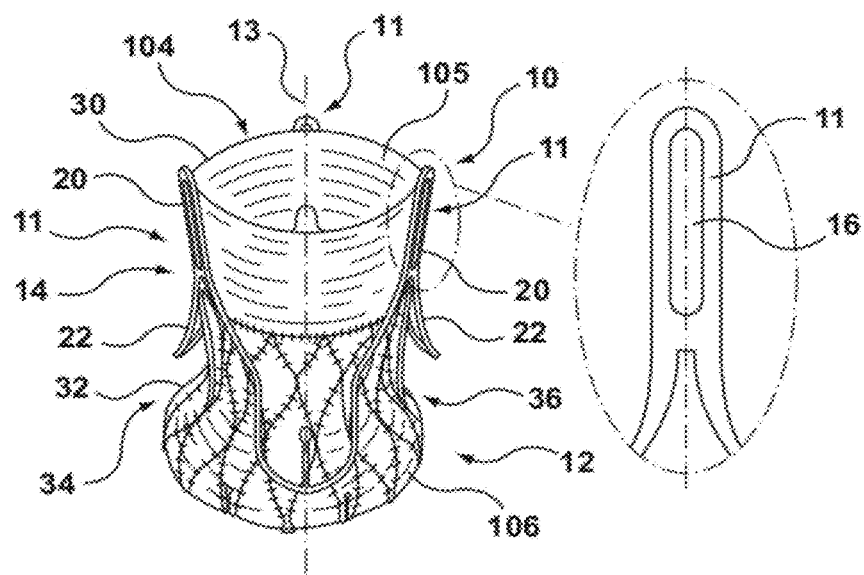
FIG. 1 is a schematic illustration of a fully-assembled valve prosthesis, in accordance with an embodiment of the present invention.

FIG. 1 is a schematic illustration of a fully-assembled valve prosthesis 10 in accordance with an embodiment of the present invention. Typically, valve prosthesis 10 comprises exactly three commissural posts 11, arranged circumferentially around a central longitudinal axis 13 of valve prosthesis 10. Valve prosthesis 10 can also be provided with two commissure posts, e.g., for placement in a native mitral valve annulus, or could be provided with more than three commissural posts. Valve prosthesis 10 further comprises a prosthetic valve 104 coupled to commissural posts 11. Valve 104 typically comprises a pliant material 105. Pliant material 105 can include, e.g., animal pericardial tissue or artificial tissue. Pliant material 105 of valve 104 is configured to collapse inwardly (i.e., towards central longitudinal axis 13) during diastole, in order to inhibit retrograde blood flow, and to open outwardly during systole, to allow blood flow through the prosthesis. For some applications, valve prosthesis 10 comprises a collapsible inner support structure 12 that serves as a proximal fixation member, and a collapsible outer support structure 14 that serves as a distal fixation member.

Figures 2A, 2B:
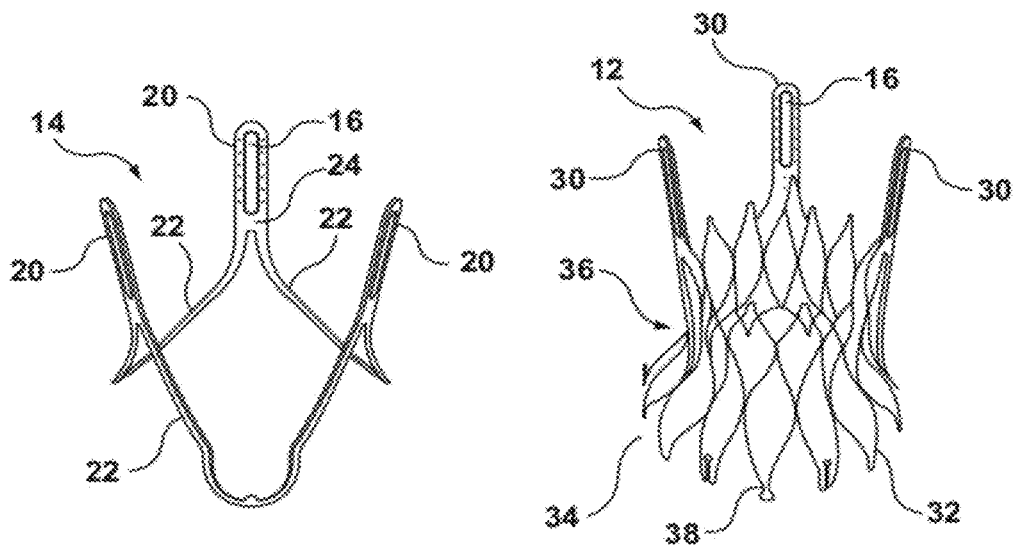
FIGS. 2A and 2B are schematic illustrations of a collapsible outer support structure and a collapsible inner support structure, respectively, prior to assembly together into the valve prosthesis of FIG. 1, in accordance with an embodiment of the present invention.

The commissural posts 11 are shaped so as define therethrough respective openings 16 that serve as radiographic identifiers during an implantation procedure, as described hereinbelow. Although FIG. 1 illustrates openings 16 on each of the three commissural posts, it is understood that openings 16 may be provided only on one or two of the commissural posts. The openings may assume any convenient shape, for example, slits, as shown in FIGS. 1 and 2A-B. In some embodiments, the openings are shaped to be reflection-asymmetric along respective post axes generally parallel with central longitudinal axis 13 of prosthesis 10 when the posts assume their collapsed position. For some applications, in addition to serving as the radiographic identifiers, openings 16 are used for coupling valve 104 to support structures 12 and 14. Although pliant material 105 of valve 104 at least partially fills openings 16, the pliant material is substantially more radiolucent than commissural posts 11, and thus does not reduce the radiographic visibility of the radiographic identifiers. One or more of posts 11 can be formed without openings 16, and the one or more posts can instead comprise radiographic identifiers comprising a material having a radiopacity different from (greater or less than) the radiopacity of posts 11, such as gold or tantalum.

Valve prosthesis 10 is configured to be placed in a native diseased valve of a subject, such as a native stenotic aortic or pulmonary valve, using a minimally-invasive approach, such as a beating heart transapical procedure, or a retrograde transaortic procedure. As used in the present application, including in the claims, a "native valve" is to be understood as including: (a) native valves that include their native leaflets, and (b) native valves in which one or more of the native leaflets have been surgically excised, are otherwise absent, or are damaged or stenosed.

Reference is made to FIG. 2A, which is a schematic illustration of collapsible outer support structure 14 prior to assembly with inner support structure 12, in accordance with an embodiment of the present invention. In this embodiment, outer support structure 14 is shaped so as to define a plurality of distal diverging strut supports 20, from which a plurality of proximal engagement arms 22 extend radially outward in a proximal direction. Engagement arms 22 are typically configured to be at least partially disposed within aortic sinuses of the subject, and, for some applications, to engage and/or rest against floors of the aortic sinuses, and to apply an axial force directed toward a left ventricle of the subject. Outer support structure 14 comprises a suitable material that allows mechanical deformations associated with crimping and expansion of valve prosthesis 10, such as, but not limited to, nitinol or a stainless steel alloy (e.g., AISI 316).

Reference is made to FIG. 2B, which is a schematic illustration of collapsible inner support structure 12 prior to assembly with outer support structure 14, in accordance with an embodiment of the present invention. For some applications, inner support structure 12 is shaped so as to define a plurality of distal diverging inner struts 30, and a bulging proximal skirt 32 that extends from the struts. A proximal portion 34 of proximal skirt 32 is configured to engage a left ventricular outflow tract (LVOT) of the subject and/or periannular tissue at the top of the left ventricle. A relatively narrow throat section 36 of proximal skirt 32 is configured to be positioned at a valvular annulus of the subject, and to engage the native valve leaflets. Inner support structure 12 comprises, for example, nitinol, a stainless steel alloy, another metal, or another biocompatible material. Inner support structure 12 also includes one or more fixation hooks 38 extending from the proximal end of inner support structure 12. Preferably, inner support structure 12 includes three fixation hooks 38. However, it is understood that fewer or greater than three fixation hooks 38 can be provided with inner support structure 12. Fixation hooks 38 extend from the proximal end of inner support structure 12 and include eyelets at their proximal end. Fixation hooks 38, which are optional, can be formed in various configurations other than that shown. For example, fixation hooks 38 can be J-shaped hooks or eyelets 38, and can take on any number of sizes or shapes while remaining compatible with the delivery methods and systems described herein.

Reference is again made to FIG. 1. Inner and outer support structures 12 and 14 are assembled together by placing outer support structure 14 over inner support structure 12, such that outer strut supports 20 are aligned with, and typically support, respective inner struts 30, and engagement arms 22 are placed over a portion of proximal skirt 32. Inner struts 30 and outer strut supports 20 together define commissural posts 11.

Although exactly three commissural posts 11 are shown in the figures, for some applications valve prosthesis 10 comprises fewer or more posts 11, such as two posts 11, or four or more posts 11.

Typically, valve prosthesis 10 further comprises a graft covering 106 which is coupled to proximal skirt 32, such as by sewing the covering within the skirt (configuration shown in FIG. 1) or around the skirt (configuration not shown). Inner support structure 12 thus defines a central structured body for flow passage that proximally terminates in a flared inlet (proximal skirt 32) that is configured to be seated within an LVOT immediately below an aortic annulus/aortic valve. For some applications, graft covering 106 is coupled at one or more sites to pliant material 105.

In an embodiment of the present invention, a portion of valve prosthesis 10 other than commissural posts 11, e.g., proximal skirt 32, is shaped so as to define openings 16 that serve as radiographic identifiers. Alternatively or additionally, the commissural posts or the selected other portion of the prosthesis comprise radiographic identifiers comprising a material having a radiopacity different from (greater or less than) the radiopacity of other portions of the prosthesis. For some applications, the radiographic identifiers are radially aligned with commissural posts 11.

Additional features of valve prostheses suitable for use in conjunction with the present invention are described in U.S. Patent Publication Nos. 2008/0071361, 2008/0071366, 2008/0071368, 2008/0071369, 2010/0131054, 2010/0137979, and 2010/0262231, each of which is incorporated, in its entirety by reference herein.

Figure 3:
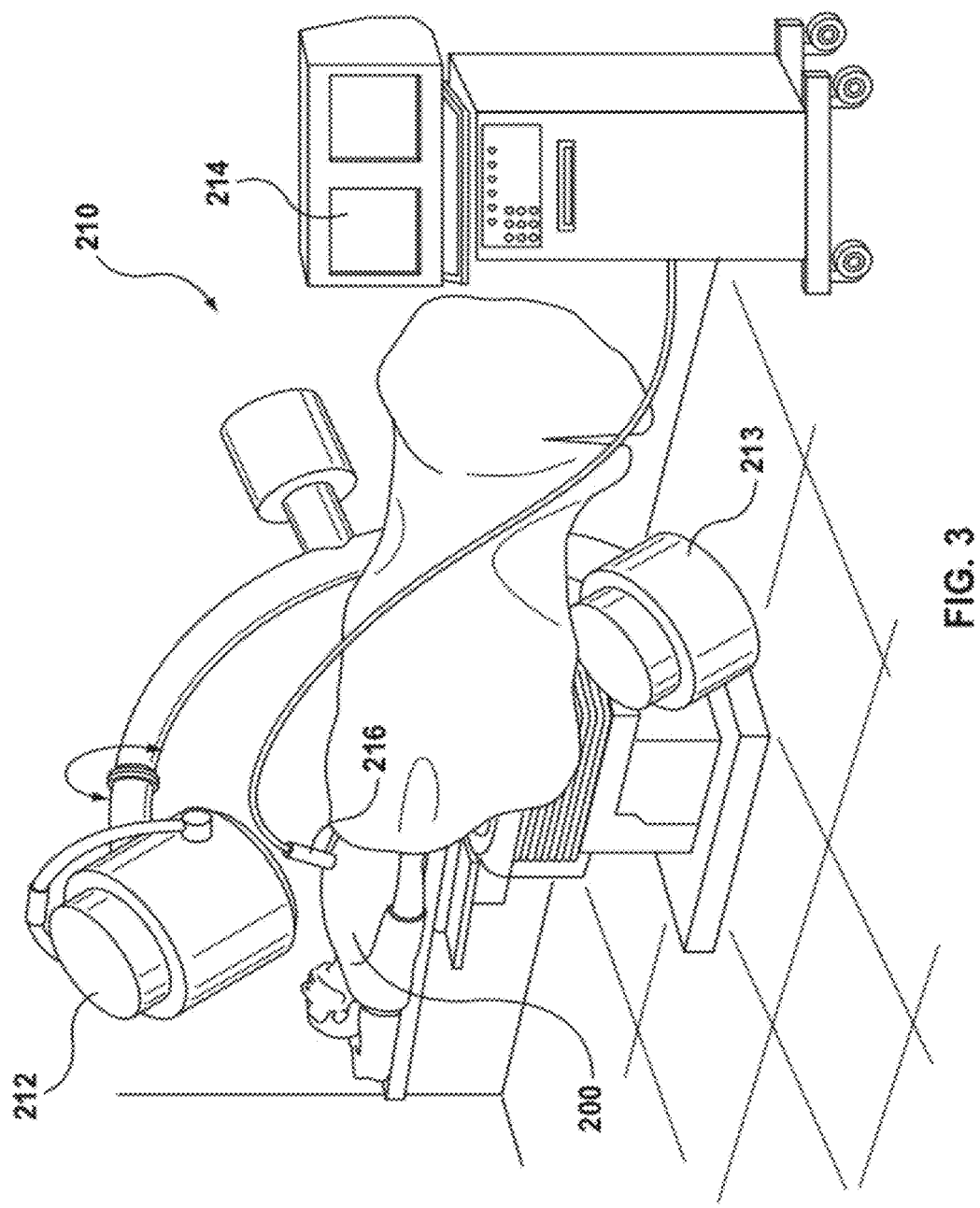
FIG. 3 is a schematic illustration of a subject undergoing a transapical or percutaneous valve replacement procedure, in accordance with an embodiment of the present invention.

FIG. 3 is a schematic illustration of a subject 200 undergoing a transapical or percutaneous valve replacement procedure in accordance with an embodiment of the present invention. A fluoroscopy system 210 comprises a fluoroscopy source 213, a fluoroscopy detector 212, and a monitor 214. Fluoroscopy source 213 is positioned over subject 200 so as to obtain a left anterior oblique (LAO) projection. Preferably, the LAO projection is at an angle between 30 and 45 degrees, such as between 30 and 40 degrees, with a 30-degree cranial tilt (for orthogonal projection of the annulus). Typically, imaging is enhanced using an ultrasound probe 216. It is understood that alternate fluoroscopy systems can be used in conjunction with the delivery systems and methods described herein.

Figure 4:
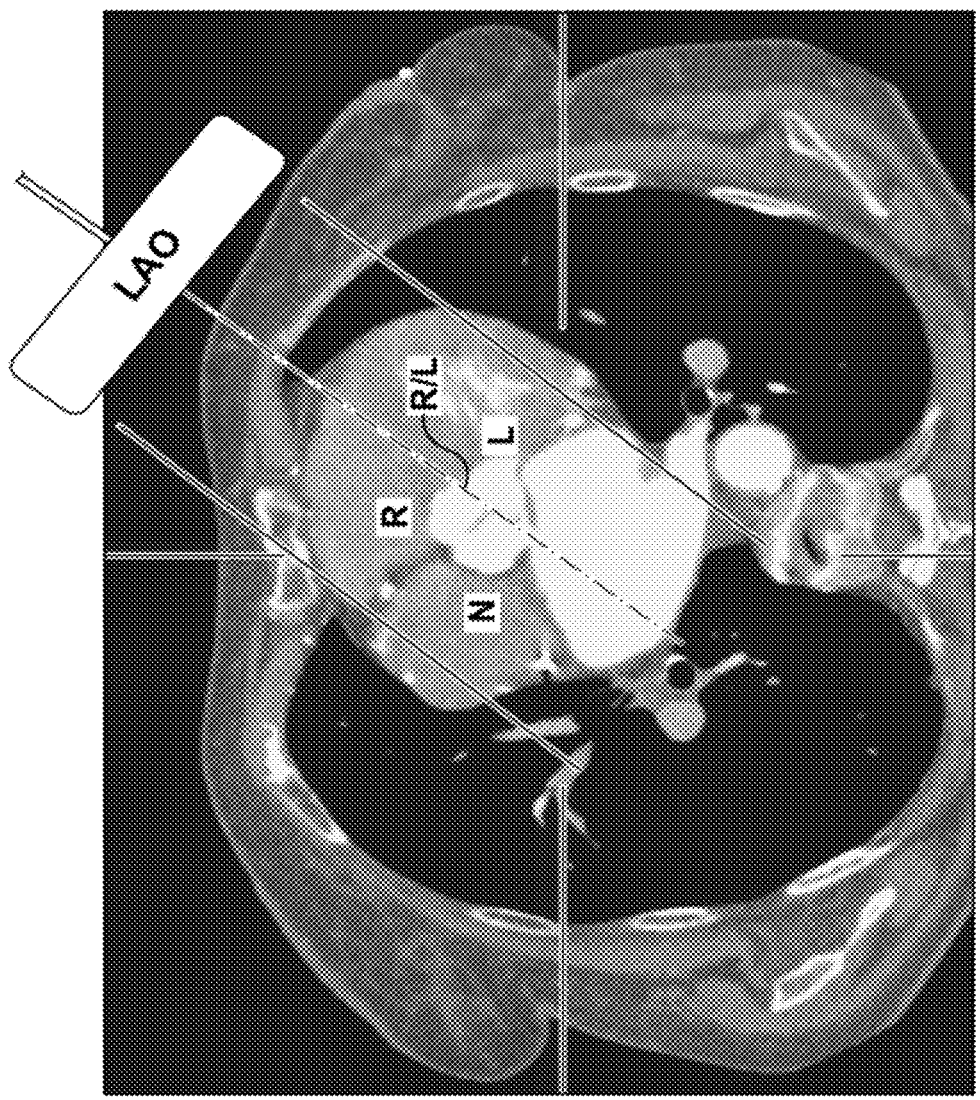
FIG. 4 shows an exemplary transverse plane MRI of an aortic root demonstrating the projection angle of a left anterior oblique projection.
Figure 5:
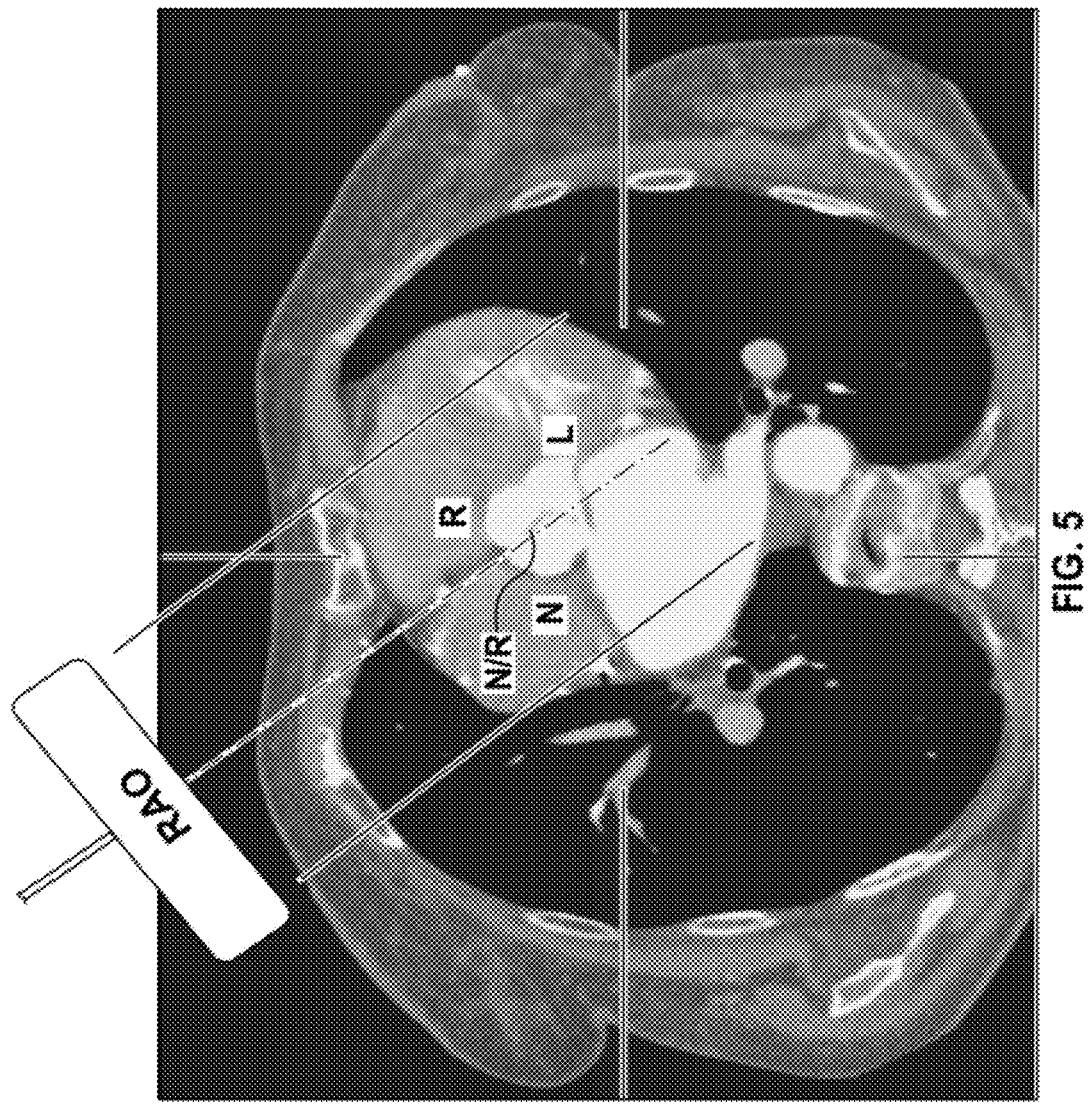
FIG. 5 shows an exemplary transverse plane MRI of an aortic root demonstrating the projection angle of a right anterior oblique projection.
Figure 6:
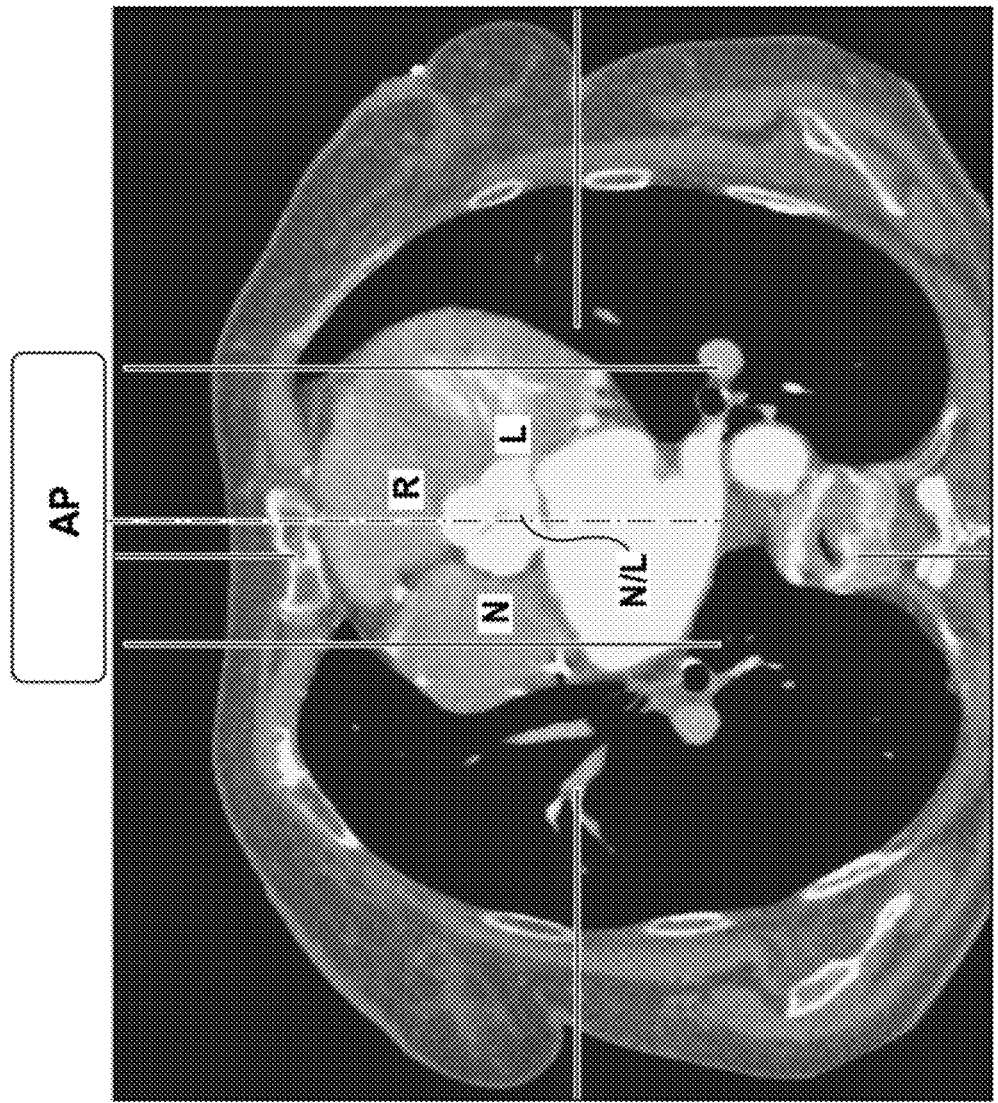
FIG. 6 shows an exemplary transverse plane MRI of an aortic root demonstrating the projection angle of an anteroposterior projection.

FIGS. 4-6 show exemplary transverse plane MRIs of an aortic root. Right coronary sinus R is generally positioned on the anterior side of the annulus. Left coronary sinus L and non-coronary sinus N are also shown. FIGS. 4-6 further illustrate a commissure R/L between the right and left coronary sinuses R and L, a commissure N/R between the non-coronary sinus N and the right coronary sinus R, and a commissure N/L between the non-coronary sinus N and the left coronary sinus L. Commissure R/L is best shown in a LAO projection, as illustrated in FIG. 4. Commissure N/R is best shown in a right anterior oblique (RAO) projection, as illustrated in FIG. 5. Commissure N/L is best shown in an anteroposterior (AP) projection, as illustrated in FIG. 6. Commissures R/L, N/R, and N/L serve as clear anatomical landmarks during the replacement procedure, enabling the physician to readily ascertain the layout of the aortic root.

Figure 7:
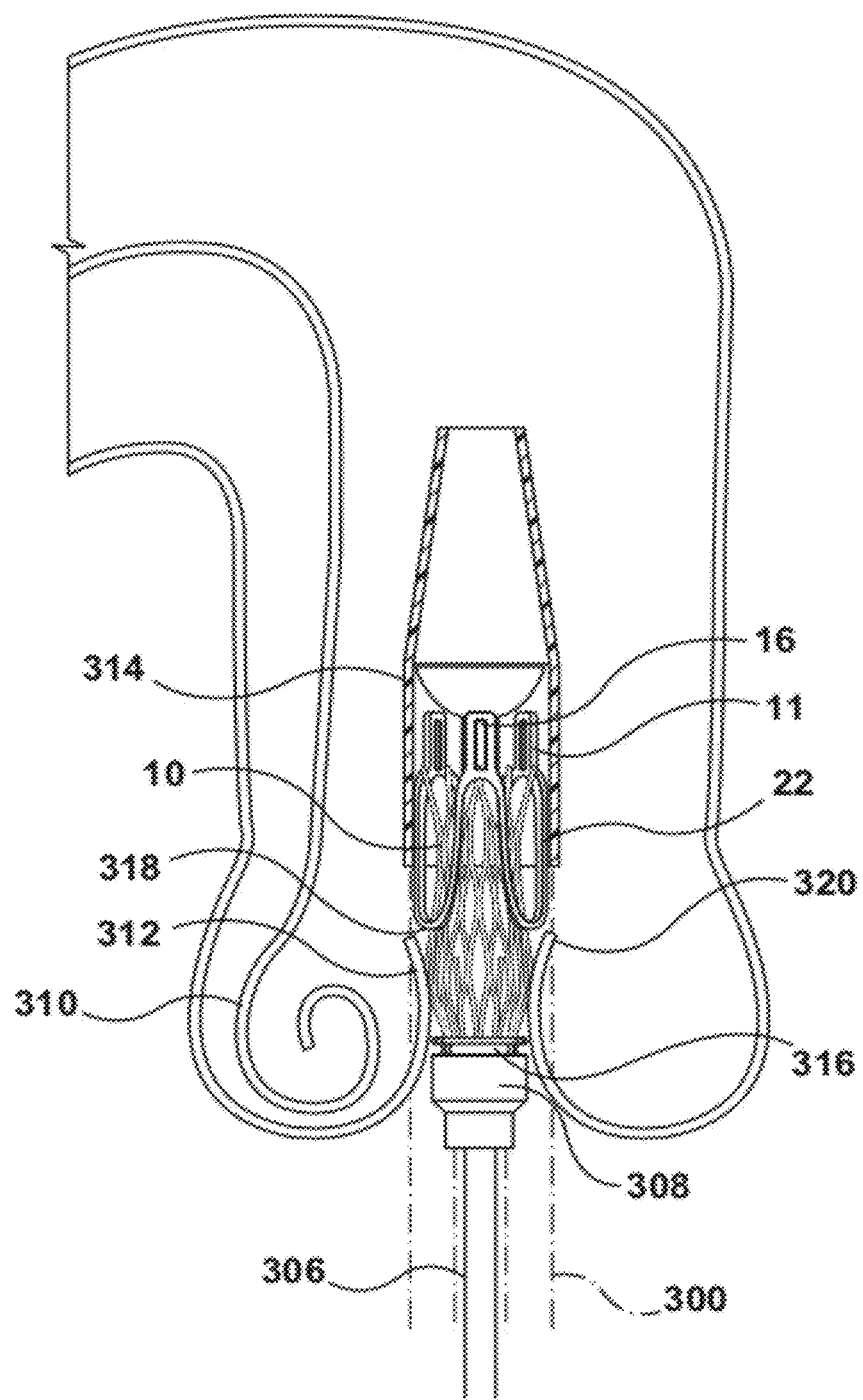
FIG. 7 illustrates a two-dimensional view of a heart valve prosthesis and delivery system according to an embodiment of the present invention at one stage of delivery.

FIG. 7 is a schematic view of valve prosthesis 10 in a collapsed, position in a catheter 300 inserted transapically and extending through a native annulus. Devices and methods for introducing a delivery system into a heart through the apex area of the heart are described by U.S. Patent Application Publication 2010/0121436, which is incorporated by reference herein in its entirely. In this embodiment, openings 16 in commissure posts 11 are shaped as slits. As noted above, openings 16 are clearly visible by fluoroscopy. Valve prosthesis 10 is contained within sleeve 314 at its distal end. Valve prosthesis 10 is held at its proximal end by valve retainer 308, which is connected to inner delivery member 306. Preferably, fixation hooks 38 on valve prosthesis 10 are engaged with valve retainer 308. An auxiliary catheter 310 is introduced into the aortic root. Auxiliary catheter 310 is preferably a pigtail catheter for introducing dyes into the aortic root area to facilitate imaging of the aortic root area. When the valve prosthesis 10 has been inserted, to the position illustrated in FIG. 7, the distal ends of engagement arms 22 are positioned downstream of the tips 320 of native valve leaflets 312. Because FIG. 7 is a two-dimensional view, only two native valve leaflets 312 are illustrated. It is also understood that the implantation devices and methods described herein can be used to implant prostheses in a native annulus that does not have three leaflets. For example, the devices and methods described herein can be used to implant prostheses in a mitral or pulmonary valve annulus. In addition, it is understood that the implantation devices and methods described herein can be used to implant prostheses in a native annulus from which one or more native leaflets have already been removed, or in which one or more of the native leaflets has been damaged.

After valve prosthesis 10 has been inserted through a native annulus, the valve prosthesis is rotationally aligned with the native commissures and sinuses of the native valve. Preferably, an RAO projection is used for the rotational alignment procedure. Once an RAO projection has been established, initial alignment proceeds generally in the manner described in U.S. Patent Application Publication 2010/0121436, which is incorporated, by reference herein in its entirely. Specifically, the physician selects one of the commissural posts 11 having a radiographic identifier, and attempts to rotationally align the selected post with one of the native commissures, such as the commissure between the left and right coronary sinuses. Because the radiographic image is two-dimensional, all of the posts appear in the image as though they are in the same plane. The physician thus cannot distinguish between two possible rotational positions of the posts: (1) the desired rotational position, in which the selected post faces the desired native commissure, and (2) a rotational position 180 degrees from the desired rotational position, in which the selected, post faces the side of the native valve opposite the desired native commissure. For example, if the desired native commissure is the commissure between the left and right coronary sinuses, in position (2) the post is rotationally aligned with the non-coronary sinus, although this undesired rotation is not apparent in the radiographic image. To ascertain whether the posts are in rotational position (1) or (2), the physician slightly rotates the valve prosthesis. If the radiographic identifier on the selected post appears to move in the radiographic image in the same direction as the rotation, the selected post is correctly rotationally aligned in the desired position (1). If, on the other hand, the radiographic identifier appears to move in the direction opposite the direction of rotation, the selected post is incorrectly rotationally aligned in position (2). To correct the alignment, the physician may rotate the valve prosthesis approximately 60 degrees in either direction, thereby ensuring that one of the two other posts is now rotationally aligned in position (1).

Figure 8:
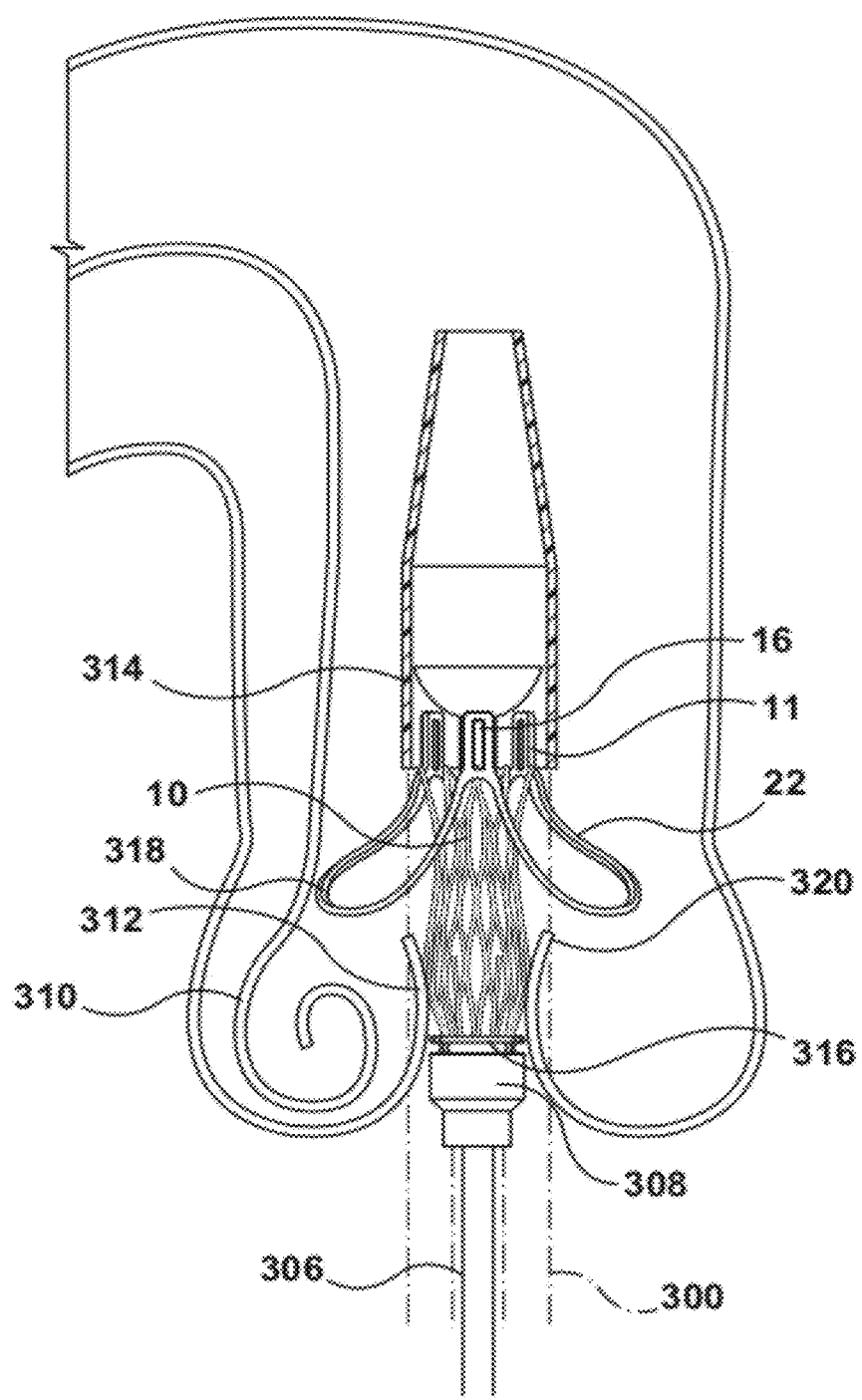
FIG. 8 illustrates a two-dimensional view of a heart valve prosthesis and delivery system according to an embodiment of the present invention at a second stage of delivery.
Figure 9:
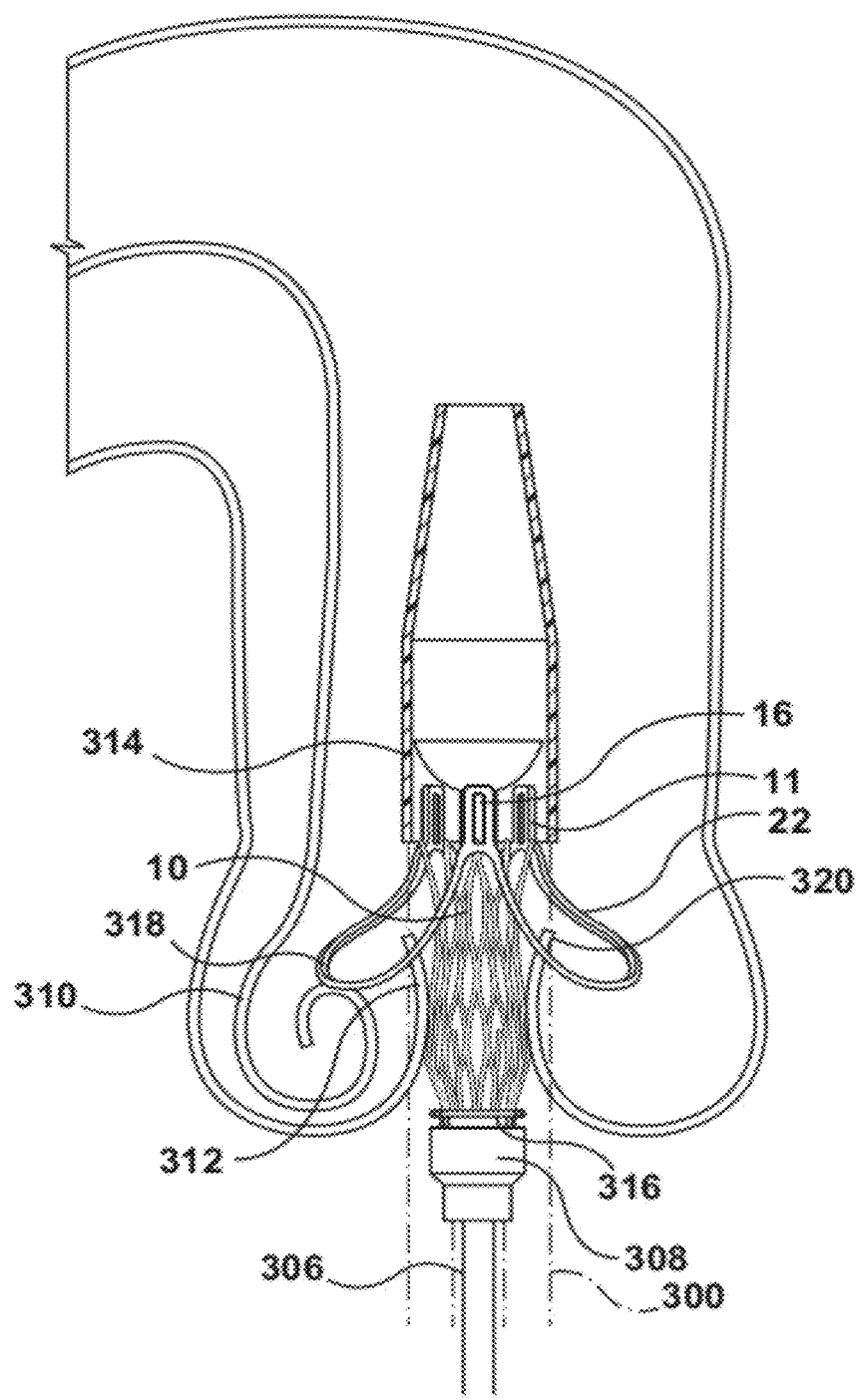
FIG. 9 illustrates a two-dimensional view of a heart valve prosthesis and delivery system according to an embodiment of the present invention at a third stage of delivery.
Figure 10:
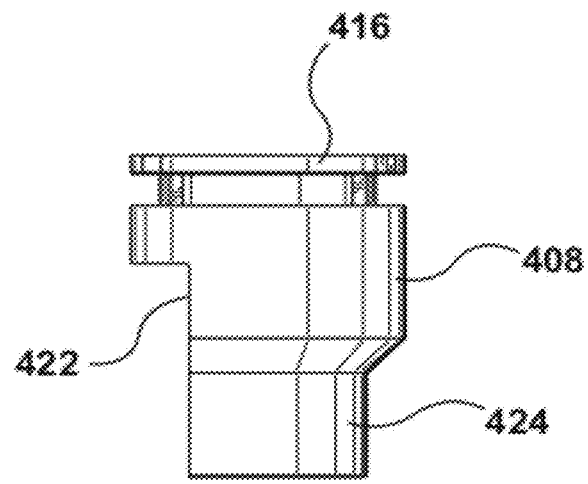
FIG. 10 is a profile view of a valve retainer according to an embodiment of the present invention.

After rotational alignment has been achieved, the physician verifies that the distal end 316 of the valve retainer 308 is still approximately at the level of the curl of the pigtail catheter 310, and that proximal ends 318 of the engagement arms 22 are still positioned downstream of the tips 320 of the native valve leaflets 312. Once this position has been confirmed, sleeve 314 is moved in a distal direction, i.e., away from valve retainer 308, to release engagement arms 22. Engagement arms 22 are configured to radially expand when released from sleeve 314, as shown in FIG. 8. Inner delivery member 306, and thereby valve retainer 308, are then retracted in a proximal direction (i.e., generally towards the apex of the heart) in order to position engagement arms 22 in their respective sinuses, as illustrated in FIG. 9. Although engagement arms 22 are shown in FIGS. 9 and 10 as not fully extending to the base of the sinuses, it is understood that the arms can be formed in a variety of shapes and lengths, and may contact the base of the sinuses and/or contact the native leaflets 312 when implanted in a native annulus. U.S. Patent Publication Nos. 2008/0071361, 2008/0071366, 2008/0071368, 2008/0071369, 2010/0131054, 2010/0137979, and 2010/0262231, each of which is incorporated, in its entirety by reference herein, disclose heart valve prostheses having engagement arms suitable for use with the present invention.

At this stage, commissural posts 11 can be released from sleeve 314 by further moving sleeve 314 in a distal direction relative to valve retainer 308. Delivery catheter 300 is then moved proximally with respect to valve retainer 308, thereby releasing the proximal skirt 32 of valve prosthesis 10. Once released, proximal skirt 32 contacts the upper ventricle of the heart below the sinuses. Proximal skirt can contact the underside of native leaflets 312 in addition to or instead of contacting the upper ventricle. Sleeve 314, valve retainer 308, and inner delivery member 306 can then be withdrawn from the heart.

Figure 11:
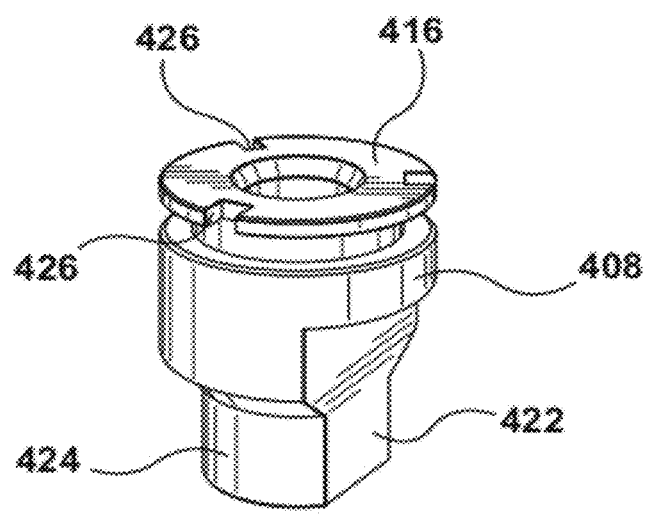
FIG. 11 is a perspective view of the valve retainer of FIG. 10.

FIG. 10 is a profile view of a valve retainer 408 according to another embodiment of the present invention. Unlike valve retainer 308, which, as shown in FIGS. 7-9, is substantially radially symmetrical, valve retainer 408 is formed with a rotational identifier on one side thereof. As shown in FIGS. 10-11, the rotational identifier can be a physical identifier such as a notch 422 formed on one side of valve retainer 408. As illustrated in FIGS. 10-11, notch 422 preferably extends from the proximal end 424 of valve retainer 408 towards distal end 416, and extends approximately 180 degrees around the outer surface of valve retainer 408. However, it is understood that notch 422 can be formed in a variety of shapes and locations consistent with the present invention. For example, notch 422 can be a narrow notch on one side of valve retainer 408, i.e., a notch that extends only a small fraction of the length of valve retainer 408. Notch 422 can extend to the proximal end 424 of valve retainer or can be formed only in the middle region of valve retainer 408. It is also understood that other physical markings can be used consistent with the present invention. The term notch is used herein to refer to any of a variety of notch, slit, groove, or other physical alteration that is visible during a fluoroscopy procedure and that provides information on the rotational alignment of the valve retainer. For example, a hole formed in the valve retainer can serve as the physical alteration.

As shown in FIG. 11, valve retainer 408 also includes three slots 426 at its distal end 416. Slots 426 are configured to receive fixation hooks 38 of valve prosthesis 10. Fixation hooks 38 serve to secure valve prosthesis 10 to valve retainer 408 when fixation hooks 38 are placed within slots 426 and valve retainer 408 is placed within a catheter, such as delivery catheter 300. As shown in FIG. 11, slots 426 are evenly positioned around the perimeter of the distal end 416 of valve retainer 408. Although three evenly spaced slots 426 are shown in FIG. 11, it is understood that fewer or more than three slots can be provided with retainer 408, and that the slots can be spaced unevenly.

Figure 12:
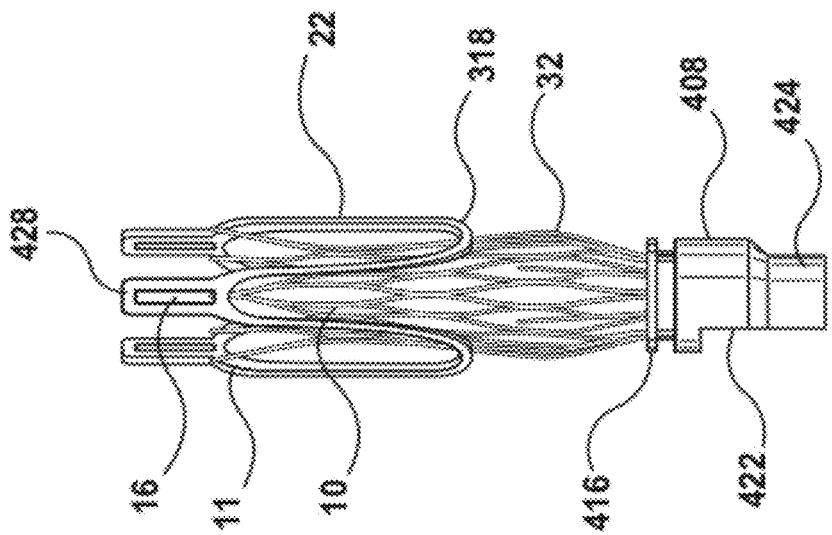
FIG. 12 illustrates a valve prosthesis in a crimped configuration connected to the valve retainer shown in FIGS. 10 and 11 at a first rotational orientation.
Figure 13:
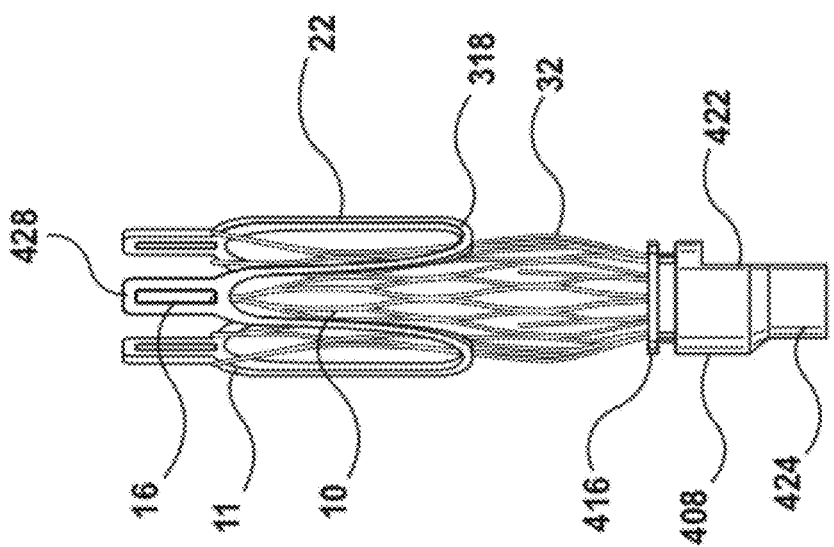
FIG. 13 illustrates a valve prosthesis in a crimped configuration connected to the valve retainer shown in FIGS. 10 and 11 at a second rotational orientation.

FIGS. 12 and 13 illustrate valve prosthesis 10, in its crimped configuration, connected to valve retainer 408. In FIG. 12, notch 422 is positioned to the right. It should be noted that the circumferential locations of the commissure posts 11 of valve prosthesis 10 relative to the fixation hooks 38 of valve prosthesis 10 are known due to the geometry of valve prosthesis 10. Specifically, commissure posts 11 and fixation hooks 38 are formed on valve prosthesis 10 such that when fixation hooks 38 are inserted, into slots 426 of valve retainer 408, the circumferential position of each commissure post 11 is known based on the geometry of valve prosthesis 10 and valve retainer 408.

Thus, when valve prosthesis 10 is loaded into valve retainer 108 and viewed in a two-dimensional profile view, such as during an angiography procedure, and, when notch 422 is visible on the right side of valve retainer 408 in the profile view, as shown in FIG. 12, a user can identify that the central commissure post 428 is rotationally positioned on the anterior side of valve prosthesis 10. This is because the location of the central commissure post 428 relative to fixation hooks 38 is known, and because the location of central commissure post 428 relative to slots 426 is known because the fixation hooks 38 are secured within slots 426. As noted above, radiographic images are two-dimensional. Because of this, absent the additional information provided by the position relationship between notch 422 and central commissure post 428, a user would be unable to distinguish between two possible rotational positions of the posts: (1) the desired rotational position, in which the selected central commissure post 428 faces the desired native commissure, and (2) a rotational position 180 degrees from the desired rotational position, in which the selected central commissure post 428 faces the side of the native valve opposite the desired native commissure.

Although a particular commissure post 11 has been identified as a central commissure post 428 for purposes of describing FIG. 12, it is understood that any of the three commissure posts 11 can serve as a central commissure post during an implantation procedure. In any particular implantation procedure, the commissure post 11 that serves as the central commissure post is determined by aligning the opening 16 of one of the commissure posts 11 with the tip of the center of coaptation 440 (see FIG. 14) of the native valve leaflets 312. It is understood that the center of coaptation 440 refers to the point where the tips of the native valve leaflets 312 meet when the native valve is in a closed position. Once the opening 16 of one of the commissure posts 11 is aligned, with the center of coaptation in a chosen radiographic view, for example, using an RAO projection, that particular commissure post 11 serves as central commissure post 428 for that procedure. It is also understood that more or fewer than three commissure posts, fixation hooks 38, and slots 426 can be utilized in the delivery devices described, herein while maintaining the advantages of the present invention. Valve retainers 408 and the delivery devices and methods described herein utilizing the described valve retainers 408 can be used to implant valve prostheses that are structurally different from the valve prostheses described, herein. For example, the delivery devices and, methods described herein can be utilized to delivery valve prostheses with no engagement arms.

Figure 14:
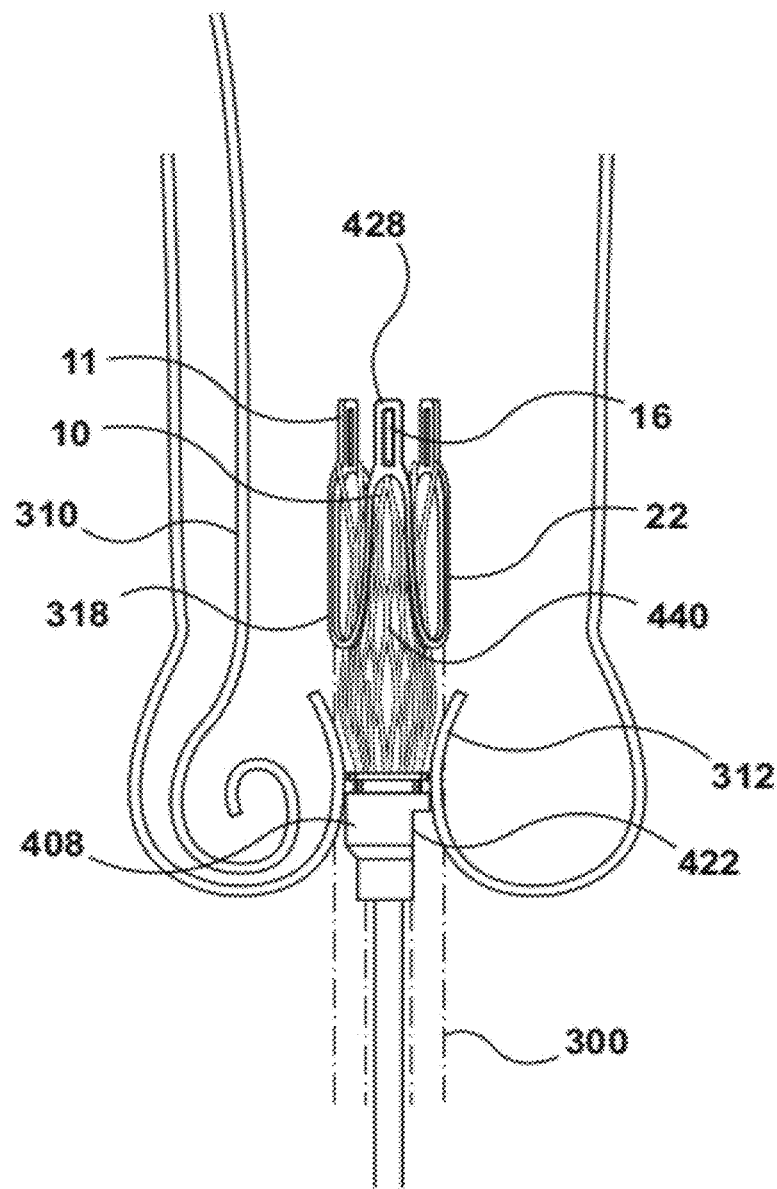
FIG. 14 illustrates a two-dimensional view of a heart valve prosthesis and delivery system according to an embodiment of the present invention at one stage of delivery.

It is understood that openings 16 may be provided only on one or two of the commissural posts. The openings may assume any convenient, shape, for example, slits, as shown in FIGS. 12-14. In some embodiments, the openings are shaped, to be reflection-asymmetric along respective post axes generally parallel with central longitudinal axis 13 of prosthesis 10 when the posts assume their collapsed position. For some applications, in addition to serving as the radiographic identifiers, openings 16 are used for coupling valve 104 to support structures 12 and 14. Although pliant material of a valve at least partially fills openings 16, the material is substantially more radiolucent than commissural posts 11, and thus does not reduce the radiographic visibility of the radiographic identifiers. As detailed above, one or more of posts 11 can be formed without openings 16, and the one or more posts can instead comprise radiographic identifiers comprising a material having a radiopacity different from (greater or less than) the radiopacity of posts 11, such as gold or tantalum.

In the profile view of loaded valve prosthesis 10 shown in FIG. 13, notch 422 of valve retainer 408 is visible on the left, i.e., rotated approximately 180 degrees from the position shown in FIG. 12. When valve prosthesis 10 is loaded into valve retainer 408 and viewed in a two-dimensional profile view, such as during an radiography procedure, and when notch 422 is visible on the left side of valve retainer 408 in the profile view, as shown in FIG. 13, a user can identify that the central commissure post 428 is rotationally positioned on the posterior side of valve prosthesis 10. This is because the location of the central commissure post 428 relative to fixation hooks 38 is known, and because the location of central commissure post 428 relative to slots 426 is known because the fixation hooks 38 are secured within slots 426.

It is understood that the rotational orientation of the identified central commissure post 428 with respect to notch 422 can be reversed, that is, notch 422 can be formed in valve retainer 408 such that when notch 422 is visible on the right side of an angiography projection, central commissure post 428 is posterior instead of anterior. In this configuration, when notch 422 is visible on the left side of an angiography projection, central commissure post 428 is anterior instead of posterior.

FIG. 14 is a schematic view of valve prosthesis 10 in a collapsed position in a catheter 300 inserted transapically and extending through a native annulus. Devices and methods for introducing a delivery system into a heart through the apex area of the heart are described by U.S. Patent Application Publication 2010/0121436, which is incorporated by reference herein in its entirely. In this embodiment, openings 16 in commissure posts 11 are shaped as slits. As noted above, openings 16 are clearly visible by fluoroscopy. Valve prosthesis 10 is contained within sleeve 314 at its distal end. Valve prosthesis 10 is held at its proximal end by valve retainer 408 which is connected to inner delivery member 306. Valve retainer 408 is provided with notch 422, which is visible on the right side of valve retainer 408. Preferably, fixation hooks 38 on valve prosthesis 10 are engaged with valve retainer 308. An auxiliary catheter 310 is introduced into the aortic root. Auxiliary catheter 310 is preferably a pigtail catheter for introducing dyes into the aortic root area to facilitate imaging of the aortic root area. When the valve prosthesis 10 has been inserted to the position illustrated in FIG. 14, the distal ends of engagement arms 22 are positioned downstream of the tips 320 of native valve leaflets 312, and therefore downstream of the center of coaptation 440. Because FIG. 14 is a two-dimensional view, only two native valve leaflets 312 are illustrated. It is understood that the implantation devices and methods described herein can be used to implant prostheses in a native annulus that does not have three leaflets. For example, the devices and methods described herein can be used to implant prostheses in a mitral or pulmonary valve annulus. In addition, it is understood that the implantation devices and methods described herein can be used to implant prostheses in a native annulus from which one or more native leaflets have already been removed, or in which one or more of the native leaflets has been damaged.

After valve prosthesis 10 has been inserted through a native annulus, the valve prosthesis is rotationally aligned with the native commissures and sinuses of the native valve. Preferably, an RAO projection is used for the rotational alignment procedure. This rotational alignment is achieved by lining up the opening 16 of one of the commissure posts 11 with the center of coaptation 440 of the native valve leaflets 312 using an RAO projection to visualize the aortic root area (this post is marked as central commissure post 428 in FIG. 14 for description purposes). Commissure N/R is the native commissure visible in an RAO projection, as shown in FIG. 5, and it is positioned on the anterior side of the heart. Thus, a user can properly align the commissure posts 11 of valve prosthesis 10 by first aligning an opening 16 of a commissure post 11 (thereafter designated central commissure post 428) with the native commissure N/R and verifying that notch 422 of valve retainer 408 is visible on the right side of the angiographic projection. As described with reference to FIG. 12, a user can identify that the central commissure post 428 is rotationally positioned on the anterior side of valve prosthesis 10 when notch 422 is visible to the right side of the profile view of valve retainer 408. Because native commissure N/R is anterior in an RAO projection, rotationally aligning central commissure post 428 to the anterior position ensures that commissure 428 is aligned with native commissure N/R. The remaining commissure posts 11 are evenly distributed around the circumference of valve prosthesis 10 to approximately match the normal spacing of the native commissures a heart such that properly rotationally aligning one commissure post 11 is sufficient to ensure that the remaining two commissure posts 11 are also properly aligned with a respective one of the remaining two native commissures R/L or N\it.

Alternately, an LAO or RAO projection can be used in conjunction with the implantation devices and methods disclosed herein. Native commissure R/L is visible when an LAO projection is utilized, as shown in FIG. 4. Therefore, when an LAO projection is used, a central commissure 428 is identified by alignment with the native commissure R/L. Because native commissure R/L is anterior in an LAO projection, central commissure 428 is properly rotationally positioned when notch 422 of valve retainer 408 is visible on the right side of valve retainer 408.

Native commissure N/L is visible when an AP projection is utilized, as shown in FIG. 6. Therefore, when an AP projection is used, a central commissure 428 is identified by alignment with the native commissure N/L. Because native commissure N/L is posterior in an AP projection, central commissure 428 is properly rotationally positioned when notch 422 of valve retainer 408 is visible on the left side of valve retainer 408.

In other embodiments, the rotational identifier of valve retainer 408 can include one or more radiopaque identifiers applied on the outer surface of valve retainer 408 or formed integrally with valve retainer 408. When a radiopaque identifier is applied to the outer surface, valve retainer 408 may or not be formed with a notch or other physical rotational identifier. For example, instead of physically notching valve retainer 408, a radiopaque identifier can be applied on one side of valve retainer 408. The radiopaque identifier can, for example, be a vertical or a dot that contrasts with the rest of valve retainer 408 during radiographic imaging. The radiopaque identifier can extend approximately 180 degrees around the outer surface of valve retainer 408. The radiopaque identifier can be positioned on valve retainer 408 in a known location relative to a commissure post of a valve prosthesis when the valve prosthesis is secured to valve retainer 408 for an implantation procedure. If the radiopaque identifier is visible when the commissure post is aligned with a native commissure, the user knows that the central commissure post is on the anterior side of the valve prosthesis. If the radiopaque identifier is not visible when the commissure post is aligned with a native commissure, the user knows that the central commissure post is on the posterior side of the valve prosthesis. As with the positioning of the notch 422 described above, the relation between the location of the radiopaque identifier and the anterior/posterior position of the commissure post can be reversed. That is, the radiopaque identifier can be positioned on valve retainer 408 such that if the radiopaque identifier is not visible when the commissure post is aligned with a native commissure, the user knows that the central commissure post is on the anterior side of the valve prosthesis.

The foregoing description of the invention has been presented for purposes of illustration and description. It is not intended to be exhaustive or to limit the invention to the precise form disclosed. Other modifications and variations may be possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. An assembly for delivering an implantable prosthesis to a target site in a body, the assembly comprising:
   an elongate inner delivery member disposed within an outer shaft, the elongated delivery member including a longitudinal axis; and
   a valve retainer connected to the elongate inner delivery member and disposed within the outer shaft during delivery to a target site in the body, wherein the valve retainer has an outer surface, wherein the valve retainer is configured to releasably secure a proximal end of a prosthesis to the elongate inner delivery member during delivery to the target site in a body, and
   wherein the valve retainer includes a rotational identifier that identifies the rotational orientation of the valve retainer around the longitudinal axis when the valve retainer is positioned proximate to the target site in the body, wherein the rotational identifier is a notch formed in the outer surface of the valve retainer such that the valve retainer is asymmetric relative to the longitudinal axis.

2. The assembly of claim 1, wherein the notch extends approximately 180 degrees around the outer surface of the valve retainer.

3. The assembly of claim 1, wherein the valve retainer includes a distal surface and a proximal surface, and wherein the distal surface includes a prosthesis retaining slot.

4. The assembly of claim 3 further comprising a heart valve prosthesis configured to be releasably secured by the valve retainer, wherein the heart valve prosthesis includes a support member and a valve member, wherein the support member includes a commissural post.

5. The assembly of claim 4, wherein the heart valve prosthesis includes a connection member, and wherein the prosthesis retaining slot of the valve retainer is configured to receive and secure the connection member of the heart valve prosthesis.

6. The assembly of claim 5, wherein the commissural post is positioned on the support member such that when the connection member is secured within the prosthesis retaining slot and the rotational identifier is visible, the commissural post has a predetermined rotational position relative to the rotational identifier.

7. The assembly of claim 6, wherein the heart valve prosthesis includes three commissural posts and three engagement arms, and wherein each of the engagement arms is configured to engage a native aortic sinus.

8. A method for implanting a heart valve prosthesis in a body, the method comprising:
   advancing a delivery system to a native valve annulus in a body, wherein the delivery system includes
      an outer shaft,
      an elongate inner delivery member disposed within the outer shaft, the elongate inner delivery member having a longitudinal axis, a distal end and proximal end,
      a valve retainer connected to the elongate inner delivery member and disposed within the outer shaft, wherein the valve retainer has an outer surface, wherein the valve retainer includes a rotational identifier that identifies the rotational orientation of the valve retainer around the longitudinal axis when the valve retainer is positioned proximate to a target site in a body, wherein the rotational identifier is a notch formed in the outer surface of the valve retainer such that the valve retainer is asymmetric relative to the longitudinal axis, and
      a heart valve prosthesis having a proximal end releasably secured to the valve retainer, wherein the heart valve prosthesis includes a commissural post;
   generating a fluoroscopic image of the heart valve prosthesis and native valve commissures; and
   rotationally aligning the heart valve prosthesis by rotating the elongate inner delivery member and the valve retainer until the commissural post is aligned with a native valve commissure and the rotational identifier is visible on a predetermined side of the valve retainer such that the rotational position of the commissural post with respect to the rotational identifier is known.

9. The method of claim 8, wherein the commissural post of the heart valve prosthesis further includes a radiographic identifier.

10. The method of claim 9, wherein the radiographic identifier is visible in the fluoroscopic image.

11. The method of claim 8, wherein the notch extends approximately 180 degrees around the outer surface of the valve retainer.

12. The method of claim 8, wherein the heart valve prosthesis includes three commissural posts and three engagement arms, and wherein each of the engagement arms is configured to engage a native aortic sinus.

13. An apparatus comprising:
   a valve prosthesis comprising:
      a prosthetic heart valve,
      a support structure, wherein the support structure includes a first material having a first radiopacity, and
      one or more radiographic identifiers, wherein the radiographic identifiers include a second material having a second radiopacity different from the first radiopacity,
   an elongate inner delivery member disposed within an outer shaft and having a longitudinal axis; and
   a valve retainer connected to the elongate inner delivery member and disposed within the outer shaft, wherein the valve retainer has an outer surface, wherein the valve retainer is configured to releasably secure a proximal end the heart valve prosthesis to the elongate inner delivery member during delivery to a target site in a body,
   wherein the valve retainer includes a rotational identifier that identifies the rotational orientation of the valve retainer around the longitudinal axis when the valve retainer is positioned proximate to the target site in the body, wherein the rotational identifier includes a notch on the other surface of the valve retainer such that the valve retainer is asymmetric relative to the longitudinal axis.

14. The apparatus of claim 13, wherein the rotational identifier includes a radiopaque material.

15. The apparatus of claim 13, wherein the valve prosthesis includes three commissural posts and three engagement arms, wherein each of the engagement arms is configured to engage a native aortic sinus.

* * * * *